United States Patent [19]

Drennan

[11] Patent Number: 5,449,339
[45] Date of Patent: Sep. 12, 1995

[54] HEEL SUPPORTING PROTECTIVE BOOT FOR BED PATIENTS

[75] Inventor: Denis B. Drennan, Evanston, Ill.

[73] Assignee: DM Systems, Inc., Evanston, Ill.

[21] Appl. No.: 239,336

[22] Filed: May 6, 1994

[51] Int. Cl.$^6$ ............................................. A61F 5/00
[52] U.S. Cl. ...................................... 602/23; 128/882
[58] Field of Search .................. 36/56, 138, 97, 81; 602/3, 5, 23, 27–29; 128/845, 846, 878, 879, 881, 882, 892

[56] References Cited

U.S. PATENT DOCUMENTS 5,143,058 9/1992 Luber et al. ............................ 602/28

*Primary Examiner*—Linda C. M. Dvorak
*Attorney, Agent, or Firm*—Mason, Kolehmainen Rathburn & Wyss

[57] ABSTRACT

A heel supporting protective boot for bed patients comprises a body formed of flexible, compressible, convoluted, non-allergenic foam material having foot and leg supporting portions for respectively supporting a patient's foot extended in an upright position and for supporting the patient's leg above the bed in a generally horizontal position with the patient's heel elevated above an adjacent bed surface. The boot includes a friction reducing material on the body below the leg and heel for providing free sliding movement of the boot over the bed surface with minimal resistance in order to avoid bunching-up of bed linens and avoiding dislocation of the patient's foot in the boot resulting in heel binding or lack of support for the sole of the patient's foot. An additional pad of a foam material may be adhesively secured to an outer surface of the boot to prevent external rotation of the leg and the pad may also be adhesively secured inside the boot adjacent the foot supporting portion to limit foot drop.

21 Claims, 3 Drawing Sheets

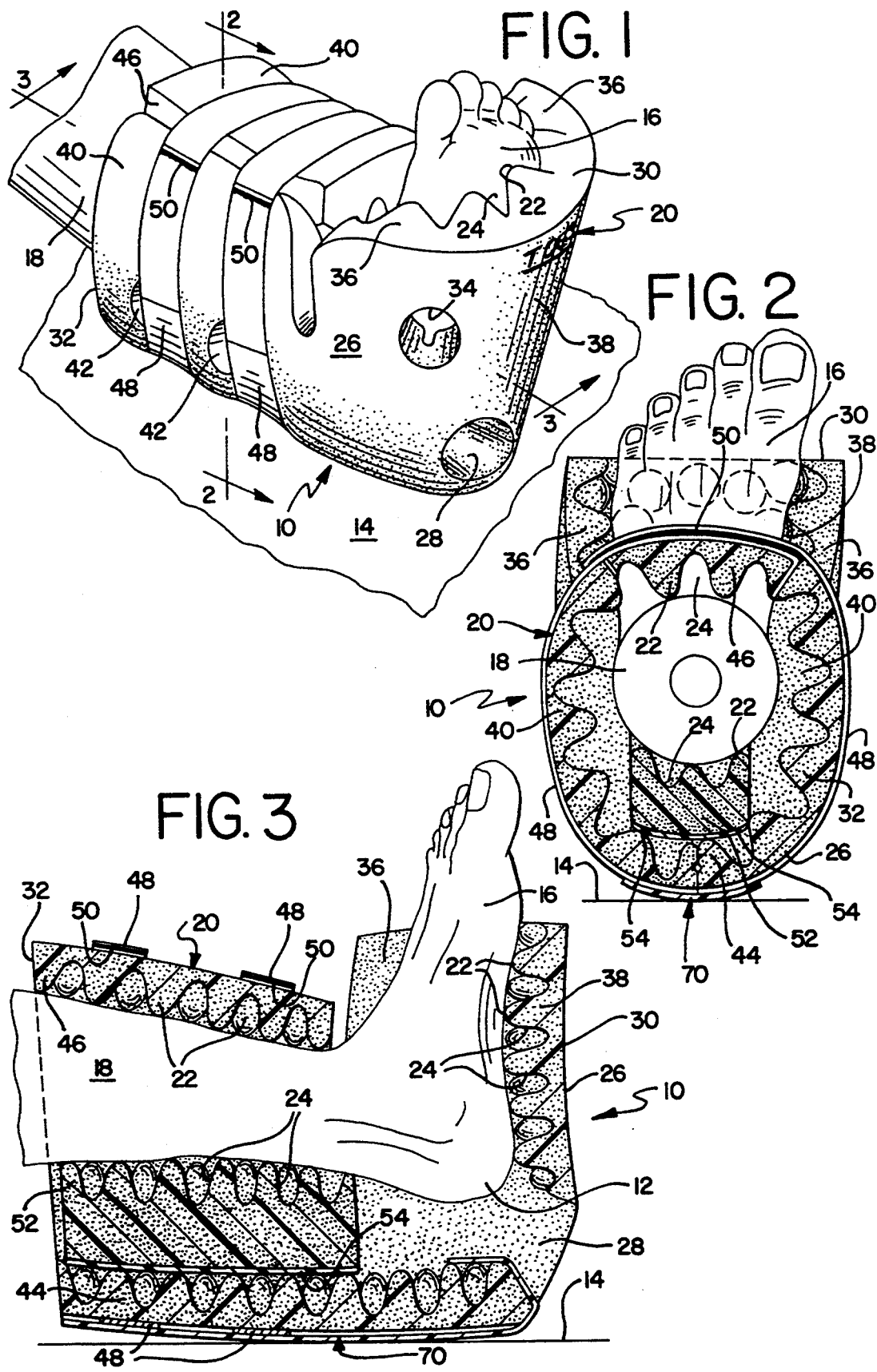

HEEL SUPPORTING PROTECTIVE BOOT FOR BED PATIENTS

BACKGROUND OF THE INVENTION

1. Field of the Invention

The present invention relates to a new and improved heel supporting protective boot for bed patients and more particularly to a heel supporting boot for bed patients having a friction reducing element beneath a patient's leg for permitting free sliding movement of the boot over the bed surface without interference or bunching-up of the bed linens. The present invention is an improvement over the heel supporting boot for bed patients disclosed and claimed in U.S. Pat. No. 4,186,738 issued Feb. 5, 1980 and incorporated herein by reference. The heel supporting protective boot of the present invention is especially designed for supporting a patient's leg at a position spaced away from the heel which is elevated above the bed surface for reducing or preventing the incidence of decubitus ulcers which are common to long term bed patients. In addition, the heel supporting protective boot is designed for preventing a malady known as foot drop and is especially adapted to provide good air ventilation with ample air circulation around the inside surface of the boot.

2. Background of the Prior Art

U.S. Pat. No. 2,911,657 to Streeter III discloses a leg and foot rest for supporting both feet of a patient with the heels in an elevated position.

U.S. Pat. No. 2,986,747 to Posey discloses a footboard designed to prevent a patient's feet from splaying apart permanently.

U.S. Pat. No. 3,011,494 to McGowan discloses a protective pad for bed patients which employs a heel cover having a surface in contact with the surface of the patient's heel.

U.S. Pat. No. 3,216,417 to Posey discloses a protective shield for bed patients adapted to protect parts of the patient's body which are commonly subjected to bed sores.

U.S. Pat. No. 3,511,233 to Holy, Jr. discloses a foot protector for supporting the foot of a bedridden patient to protect the foot from abrasion against the sheets.

U.S. Pat. No. 3,606,884 to Peter discloses a foot-boot apparatus designed to immobilize and protect the feet of bed patients to prevent bed sores, foot drop, and the like.

U.S. Pat. No. 3,691,658 to DiPerno et al. discloses an article of footwear having an inner boot and an outer shell designed to protect the foot in cold weather.

U.S. Pat. No. 3,693,619 to Williams discloses a cushion protector for bony protuberances of the body having convoluted foam adapted to fit adjacent the body of the patient.

U.S. Pat. No. 3,713,437 to Wiedmer discloses a bed shoe for preventing foot drop having means for connecting the heel portion to an exercise system so that the patient's leg may be exercised while in bed.

U.S. Pat. No. 3,936,959 to Hanson et al. discloses a ski boot with a replaceable liner having a semi-rigid shell with a two piece liner system, one section covering a forward portion of a user's foot from behind the ankle bones and a second covering the heel and Achilles' tendon areas.

U.S. Pat. No. 4,076,022 to Walker discloses a therapeutic foot and leg protector having a rigid outer shell with a soft protective liner perforated in the heel portion to allow air to enter the shell and circulate around the heel.

U.S. Pat. No. 4,150,442 to Boone discloses an elbow or heel protector including a knitted tubular sleeve and a pad formed of seamed together pieces of foam material to provide additional padding in the central portion of the sleeve to protect the patient from contact with seams on the sleeve.

U.S. Pat. No. 4,197,845 to Browning discloses a device for the prevention of decubitus ulcers on the human heel having a reservoir cushion positioned between the back of the user's ankle and the surface on which the user reposes causing the heel to remain suspended above the surface to remove pressure therefrom.

U.S. Pat. No. 4,294,022 to Stockli et al. discloses a boot for aquatic activities including a sock of elastomeric material covered with "NYLON" fabric on one or two sides and an outsole together with a back stay, toe-cap and foxing made of non-cellular rubber and directly vulcanized together as a unit on the sock.

U.S. Pat. No. 4,369,588 to Berguer now reissued as U.S. Pat. No. Re. 33,090 and reexamined thereafter, discloses an isothermic protective boot designed particularly for patients with arterial disease and having an inner lining and outer cover formed of soft non-allergenic material with a double layer of soft, flexible, compressible isothermic material between the outer cover and the inner lining.

OBJECTS OF THE INVENTION

It is an object of the present invention to provide a new and improved heel supporting boot for bed patients especially designed for eliminating the problem of decubitus ulcers of the heel, foot drop, foot splaying and other maladies commonly occurring to bed patients of extended periods.

Another object of the present invention is to provide a new and improved heel supporting boot of the character described having friction reducing means on the body for permitting free sliding movement of the boot over the bed surface with minimal resistance.

Yet another object of the present invention is to provide a new and improved heel supporting protective boot of the character described which has a friction reducing surface on the boot body for permitting free sliding movement with minimal resistance and includes means for stiffening the boot so that bunching-up does not occur in the bed linens on which the patient is reposing.

Yet another object of the present invention is to provide a new and improved heel protective boot of the character described which permits free movement of the patient's limb without any tendency of the boot to buckle because of friction with the bed surface.

Yet another object of the present invention is to provide a new and improved heel protective boot of the character described which includes an auxiliary pad for attachment to the boot in order to minimize leg roll or splaying and/or foot drop.

Still another object of the present invention is to provide a new and improved heel protective boot of the character described having opposite side portions adapted for wrapping completely around the leg of the patient away from the patient's foot to eliminate direct contact between the patient's leg and fastening straps holding the boot in place.

BRIEF SUMMARY OF THE PRESENT INVENTION

The foregoing and other objects and advantages of the present invention are accomplished in an illustrated embodiment herein comprising a new and improved heel supporting, protective boot for bed patients and the like having a body formed of flexible, compressible, convoluted, non-allergenic foam material. The unitary boot body includes a foot supporting portion and a leg supporting portion integrally joined for supporting the patient's foot extended in an upright position and for supporting the patient's leg at a level above the bed surface in a generally horizontal position with the patient's heel elevated above an adjacent bed surface. The boot is provided with a friction reducing element on the body to permit free sliding movement of the boot over the bed surface with minimal resistance so that the bed linens do not tend to bind or bunch-up and the boot itself does not tend to buckle upon attempted movement of the patient's leg. Stiffening means is provided for the body of the boot to prevent the boot itself from buckling or folding. Separate support pads of foam material with pressure sensitive adhesive on one face are available for attachment to the outside surface of the boot at appropriate positions to combat foot drop and/or foot roll or leg splay. The leg portion of the boot body includes at least one opposite side portion long enough to wrap completely around the leg of the patient at a point spaced away from the patient's foot. Adjustable length straps and/or fasteners are provided for positively securing the boot in place on a patient's leg to insure against movement of the boot out of a proper supportive position even though the patient moves.

BRIEF DESCRIPTION OF THE DRAWINGS

For a better understanding of the present invention, reference should be had to the following detailed description taken in conjunction with the drawings, in which:

FIG. 1 is a perspective elevational view illustrating a new and improved heel protecting boot constructed in accordance with the features of the present invention and shown as it is worn by a bed patient;

FIG. 2 is a transverse cross-sectional view taken substantially along lines 2—2 of FIG. 1;

FIG. 3 is a longitudinal cross-sectional view taken substantially along lines 3—3 of FIG. 1;

DETAILED DESCRIPTION OF A PREFERRED EMBODIMENT OF THE INVENTION

Figure 4:
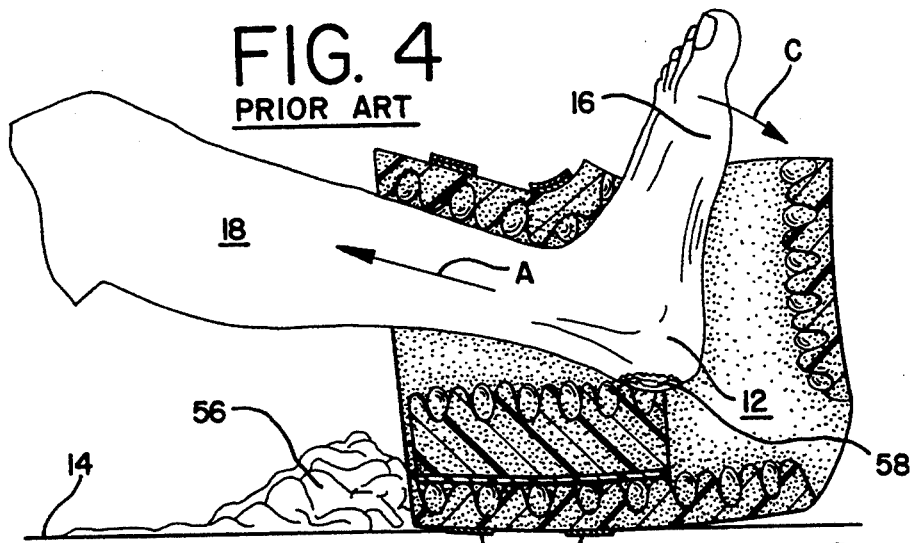
FIG. 4 is a longitudinal cross-sectional view illustrating in graphic or animated fashion, a bunching-up problem caused by excessive friction between the bottom surface of a prior art boot and the bed surface as a patient withdraws a foot upwardly toward the body causing heel binding and lack of support against foot drop.

In FIGS. 1-3 and 7 and 8 is illustrated a new and improved heel protective supporting boot 10 constructed in accordance with the features of the present invention and especially adapted for the support of a patient's heel 12 while the patient is in a generally supine position lying on a bed surface 14 or other supporting surface.

As best illustrated in FIGS. 1, 2 and 3, the boot 10 is especially designed and adapted to support a bed patient's heel 12 a short distance above the level of the bed or other surface 14 on which the patient is lying in order to provide for good air ventilation around the patient's leg 18, heel 12 and foot 16. The boot 10 supports the patient's foot 16 in an upright position (FIG. 3) so that excessive foot drop is not likely to occur. The patient's leg 18 is also supported at a level above the bed linens of the bed surface 14.

In accordance with the present invention the boot 10 includes a unitary body 20 formed from a slab of substantial thickness of open cell compressible non-allergenic resilient foam material such as polyurethane foam. The foam material is formed with a series of alternate peaks 22 and valleys 24 formed on the interior side of the boot 10 to provide for excellent air ventilation and air flow around the supported parts of the patient's foot 16 and leg 18. Heel ventilation air is supplied through a relatively large heel port or opening 28 provided adjacent the patient's heel 16. The heel port forms a junction between an upstanding, foot support portion 30 and a generally horizontally extending, leg support portion 32 integrally joined therewith.

In addition to the relatively large heel ventilation port 28, the foot portion 30 of the boot 10 is provided with a plurality of smaller ventilation openings 34 formed on opposite sides 36 thereof. These opposite sides 36 of the foot portion 30 are integrally joined with a centrally located, foot sole supporting wall section 38. The leg portion 32 includes a pair of spaced apart opposite side sections 40, at least one of which is designed to encircle and completely wrap around the patient's leg 18 as best shown in FIG. 2. The side sections 40 are formed with a plurality of ventilation ports 42 directly in communication with several of the valleys 24 on the interior surface of the foam body 20 so that air can circulate freely around the lower portions of the patient's leg 18 as well as the patient's heel 12. The opposite side sections 40 of the leg portion 32 are integrally joined with an underlying centrally positioned, leg supporting base 44 adapted to normally rest above the bed surface 14 when the patient is lying in a supine position. Usually one of the side sections 40 is dimensioned to be larger than the other so that an outer edge portion 46 thereof will extend above and wrap completely over and around an upper portion of the patient's leg 18 remote from the heel 12.

The heel supporting boot 10 may be fabricated in two or more sizes for adults and children and most other difference in sizes of particular patients in these groups can be accommodated by the amount of overlap between the upper edge portion 46 on one side section 40 over the adjacent opposite side section 40 when the boot is put in place on a patient's leg 18. In order to firmly secure the boot 10 in place to support the patient's heel 12, foot 16 and leg 18, a pair of wrap around, adjustable length, fastening straps 48 are provided at longitudinally spaced locations away from the patient's heel 12 on the body portion 32. Each strap is formed with a fastener section 50 of a type having cooperative hook and loop elements sold under the trademark "VELCRO" (FIG. 2) so that the straps can be adjusted in effective length as needed for a patient in order to firmly secure the boot 10 in place with the desired degree of snugness or tightness for patients of all different sizes. An indicator "TOES" is provided on the bottom surface of the leg support portion 32 (FIG. 1) for guidance in placement of the boot 10 on the patient.

The amount of heel elevation required for patients of various size may be attained by using one or more separate pads 52 formed of the same type of foam material as the foam body 20 of the support boot 10. The pads 52 are generally rectangular in shape and are packed inside the boot 10 positioned to lie one above the other on the base section 44 of the leg portion 32 between the opposite side sections 40 as shown. Normally a top one of the pads 52 is removed for patients of normal size. Each pad 52 includes a generally flat surface on one face and an undulating surface on an opposite face having a plurality of peaks 22 and valleys 24 for providing good circulation of air around the patient's leg when the pads are in place as shown in FIGS. 2 and 3. The flat face of each pad 52 is provided with a layer of pressure sensitive adhesive 54 which is normally covered and protected by an air impervious film of thin, flexible plastic material until the pad is ready to be permanently affixed in position on the boot 10.

Figure 5:
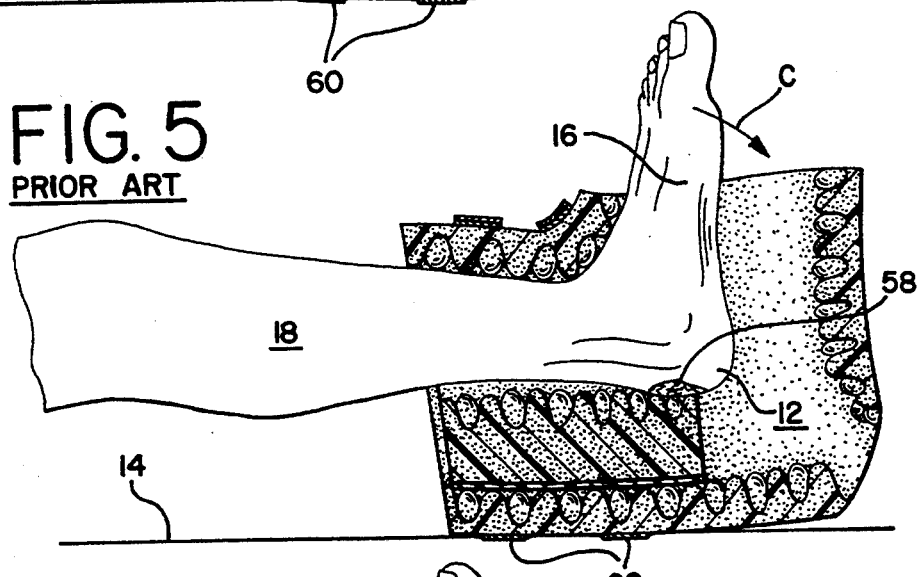
FIG. 5 is another animated illustration showing a patient's foot out of a proper supporting position in a prior art boot wherein proper support by a foot portion of the boot to preclude foot drop is not being provided.
Figure 6:
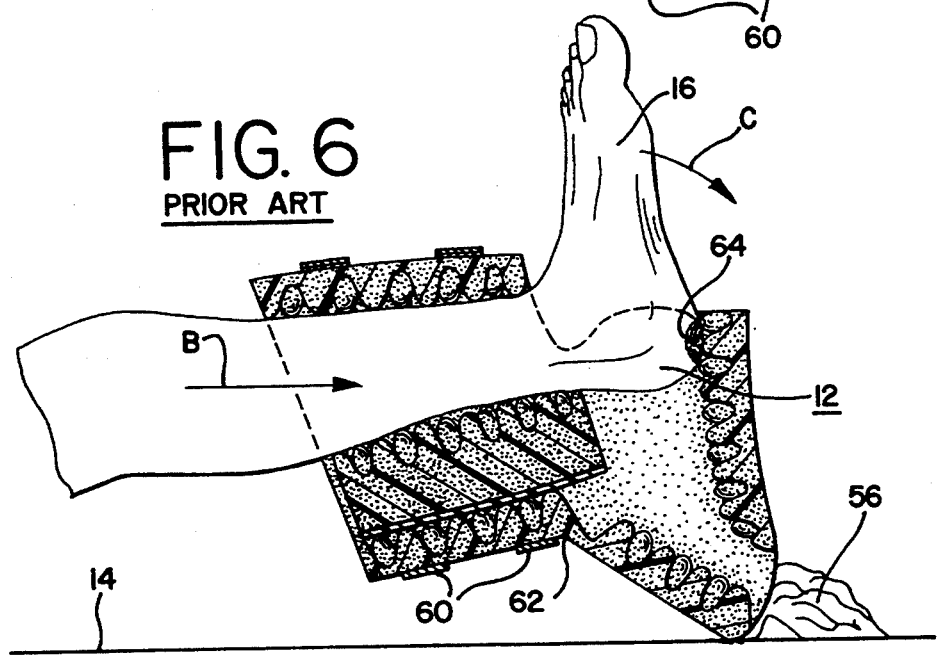
FIG. 6 is another animated illustration showing a prior art boot when the leg is thrust downwardly and away from the patient's body causing bunching-up of the bed surface resulting in the patient's foot extending too far out of the boot for proper support.

Referring now to FIGS. 4, 5 and 6, one problem with prior art boots has been that when a patient draws a leg 18 upwardly toward the body as shown by the arrow A in FIG. 4, because of excessive friction between the bottom of the boot and the surface of the bed sheet 14, bunching-up of the sheet tends to occur as shown by the reference numeral 56. This makes it difficult for a patient to move his foot 16 and because of excessive friction and the bunching-up 56, the travel of the boot is less than that of the foot 16 and the sole of the foot moves away from the support offered by bottom wall of the boot. In addition, the patient's heel 12 is moved into direct or binding contact with the supporting surfaces of the interior boot as indicated by the reference numeral 58. This condition can contribute to decubitus ulcers of the heel and also fails to protect against foot drop (arrow C) because of the lack of support against the sole surface of the patient's foot 16.

Excessive friction between the bottom of the boot may be caused by surface roughness, sharp edges or corners and by straps 60 or the like tending to restrict free movement of the boot in response to efforts of the patient to move. When a patient's leg 18 is at rest after withdrawal upwardly as shown in FIG. 5, the heel 12 may still remain in contact with the interior surface of the boot in a binding confrontation as shown by the number 58. Thus protection against decubitus ulcers is lessened and the lack of support against the sole of the foot could permit foot drop to occur even at rest because of previous malpositioning of the boot after a patient's attempt at leg movement.

On the other hand, should the patient extend his leg 18 in a direction downwardly and away from the body as indicated by the arrow B in FIG. 6, excess friction or interference between the lower corner of the boot again could cause bunching-up of the bed linens as shown by the numeral 56 preventing or limiting further travel of the boot and causing the boot to buckle or bend as shown at an area adjacent a crease line 62. In this condition, the heel 12 then strikes the lower foot support portion and heel binding occurs as indicated by the numeral 64. When this condition occurs, the patient's heel 12 is no longer free of pressure from the boot and at the same time, the upper end of the patient's foot 16 is completely unsupported so that foot drop can occur as indicated by the arrow C.

These foregoing problems are corrected in accordance with the present invention by the heel protective boot 10 which employs an elongated, relatively stiff, friction reducing pad 70 extending the length of the boot from the heel port 28 to the upper end of the leg support section 32. The pad is formed of woven strands of a low friction, "Tricot" material stitched in place around the periphery thereof. The relatively slick surface of this material insures that the boot 10 may slide freely and easily over the bed surface 14 in any direction without bunching-up of the bed linens as shown in FIGS. 4 and 6. Moreover, free movement of the boot 10 allows the patient to exercise even when confined to the bed simply by moving the legs up and down and sideways without fear of dislodging the boot from a proper, heel supportive position on the patient's limb. It should also be noted that the elongated, friction reducing pad 70 is positioned on the outside surface of the boot 10 and covers up the binding straps 48 so that a smooth, low-friction surface is presented that guarantees free and easy movement of the boot over the bed surface 14 without bunching-up of the bed linens, binding of the patient's heel 12, or crimping or bending of the boot (FIG. 6) because of excess friction or interference.

The pad 70 provides sufficient longitudinal stiffness for the boot so that crimping or bending of the boot forming a crease does not occur. The pad 70 extends fully into the heel port 28 as shown in FIG. 3, and is secured to the interior surface of the base section 44 below the patient's heel 12. This provides a smooth outer surface at the corner or junction between the upstanding foot supporting portion 30 and the horizontally extending leg support portion 32 of the boot body 20.

Figure 7:
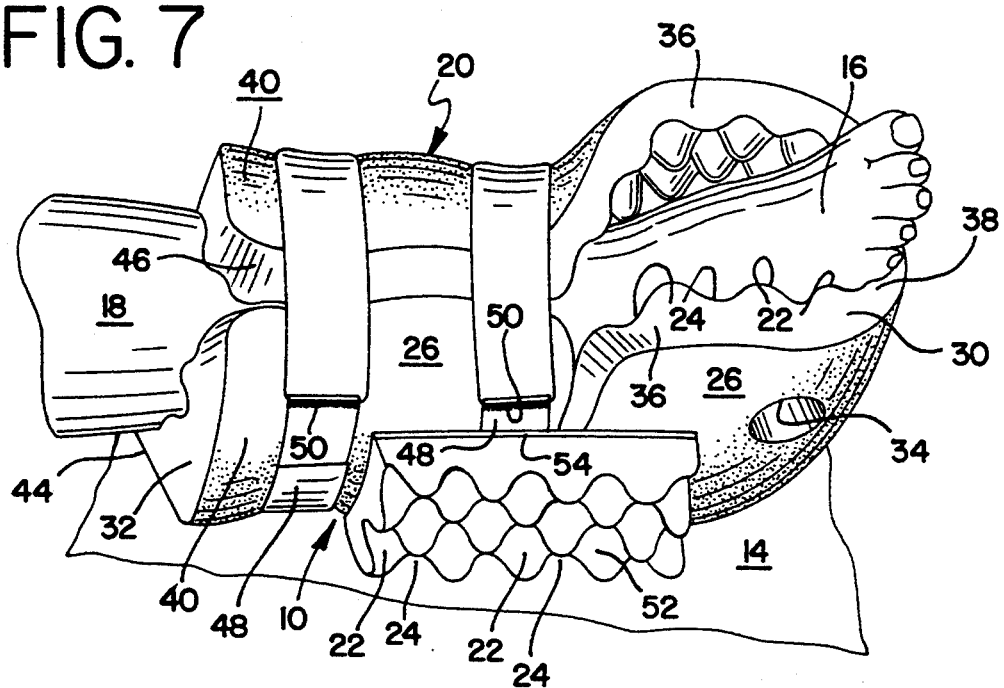
FIG. 7 is a perspective view illustrating a feature of the heel protecting boot of the present invention showing a separate pad attached to an outer surface of the boot in a position for preventing excessive external rotation of a patient's foot.
Figure 8:
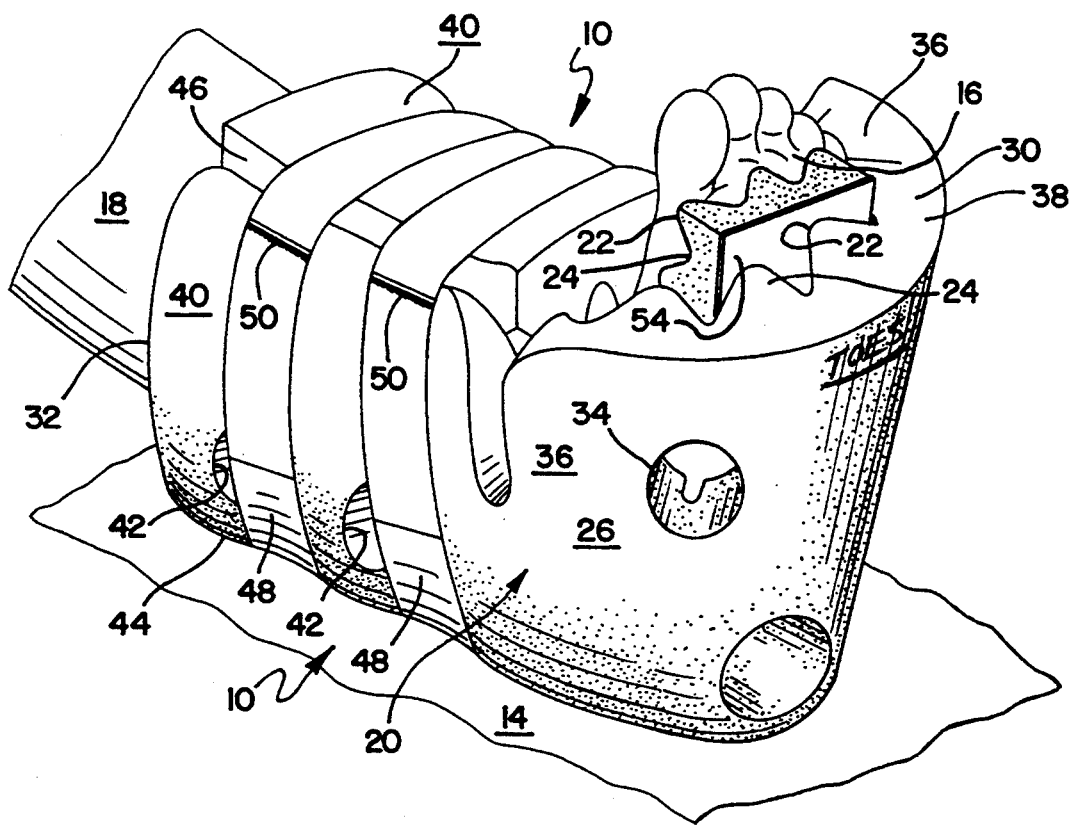
FIG. 8 is a perspective elevational view of a heel protecting boot in accordance with the invention illustrating a separate pad attached to an inner surface of the boot in a position for providing greater stiffening of the foot support portion of the boot to better resist foot drop.

When more stiffness is needed for the upstanding foot portion 30 to further guard against foot drop, one of the separate pads 52 may be fixed to the inner surface of the base of the foot support section 30 as shown in FIG. 8. The pad 52 is placed inside the foot portion 30 with the convoluted foam surface facing the patient's foot 16 and is adhesively secured in place. The pad 52 usually extends outwardly above the level of the foot support section 30 to provide added forefoot support. The adhesive layer 54 of the pad 52 is exposed by peeling away the covering film and the pad is then pressed against the surface of the foot portion 30 until the pressure sensitive adhesive sets sufficiently providing increased stiffness and support to protect against foot drop. One of the separate pads 52 may also be utilized to limit or prevent external rotation of the patient's leg 18 and foot 16. This is accomplished as shown in FIG. 7 by adhesively affixing one or more of the pads 52 to a side surface of the boot 10 at an appropriate location.

The boot 10 provides a much improved performance in permitting free, sliding movement of the boot over a bed surface 14 without substantial friction or interference, thus eliminating bunching-up of the bed linens 14. The boot 10 is easier to maintain in proper position on the leg 18 and the foot 16 of a patient and the straps 48 with adjustable length, "Velcro" fastener section 50 permit a complete wrapping around the leg 18 of an upper portion 46 of the leg support section 32 of the boot. Direct engagement between the straps 48 and the leg 18 is eliminated and engagement between the straps and the bed surface 14 is also eliminated by the underlying low friction pad 70 which also provides additional longitudinal stiffness for the boot. The boot 10 thus provides many improved characteristics over prior art boots and eliminates or reduces the problems which are pictorially set forth in FIGS. 4, 5 and 6 and discussed herein.

Obviously, many modifications and variations of the present invention are possible in light of the above teachings. Thus, it is to be understood that, within the scope of the appended claims, the invention may be practiced otherwise than as specifically described above.

What is claimed and desired to be secured by Letters Patent of the United States is:

1. A heel supporting protective boot for bed patients, comprising:
   a body formed of flexible, compressible, convoluted, non-allergenic foam material having foot and leg supporting portions for respectively supporting a patient's foot extending in an upright position and supporting the patient's leg away from the patient's bed in a generally horizontal position with the patient's heel elevated above an adjacent bed surface; and
   friction reducing means on an outer surface of said body for permitting easy sliding movement of said boot over said bed surface with minimal resistance, said friction reducing means extending substantially the entire length of said leg supporting portion between opposite ends positioned so as to rest below a back side of the patient's leg and heel and comprising a woven stranded material.

2. The boot of claim 1, including:
   elongated stiffening means extending along the length of said body for preventing buckling of said boot between said foot and leg supporting portions thereof.

3. The boot of claim 2, wherein:
   said stiffening means includes pad means between said body and said friction reducing means.

4. The boot of claim 1, wherein:
   said friction reducing means includes a layer of tricot material formed of woven low friction strands.

5. The boot of claim 4, wherein:
   said layer of tricot material extends longitudinally of said body on said leg portion and is secured in place there on a row by stitching around a periphery of said layer.

6. The boot of claim 4, including:
   a pad of stiffening material between said body and said layer of tricot material.

7. The boot of claim 1, wherein:
   said leg portion of said body includes opposite side portions for wrapping completely around the leg of said patient away from the foot; and
   strap fastening means spaced outwardly of said patient's leg for securing said side portions of said body in wrapped relation around said patient's leg.

8. The boot of claim 7, wherein:
   one of said side portions of said body is larger than the other to cover over the anterior portion of the patient's leg for preventing engagement of said strap fastening means with the patient's leg.

9. The boot of claim 1, including:
   a separate support pad means of flexible, compressible, non-allergenic material for supporting said patient's leg away from the heel in said boot; and
   adhesive means for securing said pad means in said boot body in a supporting position beneath said patient's leg and for securing said pad means to an outside surface of said boot body to minimize leg roll or foot drop.

10. The boot of claim 9, wherein:
    said adhesive means includes a layer of adhesive material between said pad means and said boot body that is protected by a cover sheet that is removable to permit adhesive attachment between said pad means and said boot body.

11. The boot of claim 1, including:
    indicator means for guiding proper placement of the boot on a patient's foot.

12. The boot of claim 2, wherein:
    said boot body is formed with a ventilation opening between said foot portion and said leg portion below the patient's heel; and
    said stiffening means extends to said ventilation opening.

13. A heel supporting protective boot for bed patients and the like, comprising:
    a boot body formed from a sheet of flexible, compressible, non-allergenic foam material with integral foot and leg supporting portions for respectively supporting a patient's foot extending in an upright position and for supporting the patient's leg in a position spaced away from the patient's heel in a generally elevated horizontal position above an adjacent bed surface;
    friction reducing means on an outer surface of said leg portion of said boot body positioned so as to rest underneath the patient's leg for permitting free sliding movement of said boot over said bed surface, said friction reducing means comprising layer of woven stranded material extending between opposite ends of said leg portion and generally conforming to said outer surface; and
    elongated stiffening means extending along the length of said boot body for preventing buckling of said boot between said foot and leg supporting portions thereof.

14. The boot of claim 13, wherein:
    said stiffening means includes pad means between an outer surface of said boot body and said friction reducing means.

15. The boot of claim 13, wherein:
    said friction reducing means includes a layer of tricot material formed of woven strands having an outer surface with a low coefficient of friction.

16. The boot of claim 15, wherein:
    said layer of tricot material extends longitudinally of said body on said leg portion and is secured in place there on a row by stitching around a periphery of said layer.

17. The boot of claim 13, wherein:

said stiffening means includes a pad of stiffening material sandwiched between said boot body and said layer of tricot material.

18. The boot of claim 13, including:

a separate support pad means of flexible, compressible, non-allergenic material for supporting said patient's leg away from the heel in said boot; and adhesive means for securing said pad means inside said boot body in a leg supporting position beneath the patient's leg, in a foot supporting position adjacent said foot portion for limiting foot drop and for securing said pad means to an outside surface of said boot body to minimize external leg roll.

19. The boot of claim 18, wherein:

said adhesive means includes a layer of adhesive material between said pad means and said boot body that is protected by a cover sheet that is removable to permit adhesive attachment between said pad means and said boot body.

20. The boot of claim 13, wherein:

said leg portion of said boot body includes opposite side portions for wrapping completely around the leg of the patient away from the patient's foot; and strap fastening means spaced outwardly of the patient's leg for securing said side portions of said boot body in wrapped relation around the patient's leg.

21. The boot of claim 20, wherein:

one of said side portions of said boot body is larger than the other to cover over the front side of the patient's leg for preventing engagement of said strap fastening means with the patient's leg.

* * * * *